US012761205B2

(12) United States Patent
Marshall

(10) Patent No.: US 12,761,205 B2
(45) Date of Patent: Oct. 13, 2026

(54) METHODS OF EVALUATING CONCRETE SAMPLES USING MULTI-PHASE ANALYSIS

(71) Applicant: Missouri Highways and Transportation Commission, Jefferson City, MO (US)

(72) Inventor: Robert Sam Marshall, Jefferson City, MO (US)

(73) Assignee: Missouri Highways and Transportation Commission, Jefferson City, MO (US)

(*) Notice: Subject to any disclaimer, the term of this patent is extended or adjusted under 35 U.S.C. 154(b) by 317 days.

(21) Appl. No.: 18/434,320

(22) Filed: Feb. 6, 2024

(65) Prior Publication Data

US 2025/0251386 A1 Aug. 7, 2025

(51) Int. Cl.
*G01N 33/38* (2006.01)
*G01N 1/40* (2006.01)
*G01N 1/44* (2006.01)

(52) U.S. Cl.
CPC ......... *G01N 33/383* (2013.01); *G01N 1/4055* (2013.01); *G01N 1/44* (2013.01)

(58) Field of Classification Search
CPC ....... G01N 1/4055; G01N 33/383; G01N 1/44
See application file for complete search history.

(56) References Cited

U.S. PATENT DOCUMENTS 4,157,998 A * 6/1979 Berntsson ........... C04B 20/1018 106/668
10,647,026 B2 * 5/2020 Jordan ................. G01N 33/383
11,142,667 B2 * 10/2021 Dongre ...................... E01C 7/18
12,247,970 B2 * 3/2025 Arnold ................ C04B 40/0032
2011/0004332 A1 * 1/2011 Andersen ............ C04B 40/0032 700/265
2021/0319377 A1 * 10/2021 Dittrich .................. G01N 21/65
2022/0317109 A1 10/2022 Arnold et al.

FOREIGN PATENT DOCUMENTS

CN 109596547 A 4/2019
CN 112710650 A 4/2021
EP 4112577 A1 * 1/2023 ............. C04B 7/246
JP 2008224649 A * 9/2008
WO WO-2022139301 A1 * 6/2022 ............. G01N 17/00

* cited by examiner

*Primary Examiner* — Octavia Hollington
(74) *Attorney, Agent, or Firm* — Armstrong Teasdale LLP

(57) ABSTRACT

A method of evaluating a concrete sample includes providing the concrete sample including a main body made of a concrete material including an aggregate and a paste, isolating a portion of the aggregate from the main body, and isolating a portion of the paste from the main body and the isolated portion of the aggregate. The method also includes separately analyzing two or more of the isolated portion of the aggregate, the isolated portion of the paste, and the main body. Based on the analyses, the method includes determining whether the concrete material includes one or more sources of failure.

16 Claims, 2 Drawing Sheets

METHODS OF EVALUATING CONCRETE SAMPLES USING MULTI-PHASE ANALYSIS

FIELD

The field of the disclosure relates to methods of evaluating concrete core samples and, more particularly, to methods of evaluating concrete core samples using chemical analysis of a main body, an aggregate, and a paste or binder of the concrete core sample to identify actual and/or potential sources of failure.

BACKGROUND

Concrete is widely used for the construction of infrastructure, including highways, bridges, residential and commercial buildings, dams, electric power generation plants, and nuclear power plants. Concrete is typically formed as a hardened composite material from a heterogeneous mixture of fine and/or coarse aggregate, cement, and water. The constituents may make the concrete susceptible to various deterioration mechanisms including corrosion of rebar reinforcement, sulfate attack, alkali-aggregate reactions, freeze-thaw durability issues, efflorescence, radiation, elevated heat of hydration, salt crystallization, and microbiological attack. Pores or voids formed in the concrete because of entrapped air during mixing and setting may also have negative effects on the durability and other properties of the concrete. Concrete is a highly alkaline environment where cement alkalis (e.g., sodium oxide and potassium oxide) may react with the silicon dioxide of the fine and/or coarse aggregate in the concrete and deteriorate the structural integrity of the concrete. In addition, other factors may lead to concrete deterioration thus jeopardizing the serviceability and safety of structures. Ultimately, this could lead to economic losses, catastrophic failures, and fatalities.

In this regard, various test methods have been developed that are used to evaluate the concrete used in such structures to determine whether the concrete is suitable for its effective service life or whether the concrete includes sources of failure that may ultimately lead to concrete deterioration. Some such test methods include evaluating the alkali-aggregate reactivity in the aggregate. Alkali-aggregate reactions occur between alkaline solutions (typically sodium and potassium hydroxides derived from the cement) in the cement paste matrix, and aggregate particles of particular but nevertheless somewhat variable compositions and textures, which may chemically alter the aggregate, causing it to expand or contract in size and ultimately leading to spalling, cracking, and/or loss of strength in the concrete. There are two primary types of alkali-aggregate reaction mechanisms that have been observed in concrete: alkali-silica reaction (ASR) and alkali-carbonate reaction (ACR). ASR may occur when hydroxyl ions from the cement react with siliceous phases (e.g., amorphous silica) in the fine and/or coarse aggregate to form a viscous, hygroscopic silicate gel (e.g., sodium silicate, $Na_2SiO_3$) that can absorb moisture from the surrounding environment (e.g., forming sodium silicate hydrate, $Na_2SiO_3 \cdot nH_2O$). Over time, in the presence of sufficient moisture, the gel expands such that the expansive pressure from the gel creates cracks in the concrete. ACR causes expansion within the aggregate due to the breakdown of dolomitic limestones. Because the expansion occurs within the aggregate, ACR can result in localized aggregate cracking or, if the reaction occurs on a large enough scale, cracking, and deterioration of the concrete mass overall. The scale and severity of the reaction depend on the alkali content of the concrete mixture, in particular the cement and the chemical composition of the applied aggregate.

Existing test methods that are used to evaluate concrete may include determining the likelihood for concrete failure due to these AARs, however such test methods remain limited. For example, some such test methods may require expensive instrumentation and equipment such as a scanning electron microscope to determine whether the compositional make-up of the aggregate increases the alkali-aggregate reactivity of the concrete. Other test methods may focus on the aggregate phase of the concrete, and exclude the paste and/or the pores, which may provide further insight, if applied, into the alkali-aggregate reactivity of the concrete and its potential for failure.

Accordingly, there is a need to address the limitations associated with existing test methods for evaluating concrete and to provide test methods that provide a comprehensive chemical analysis of the concrete that facilitates accurately predicting concrete failure and/or determining actual sources of failure in a cost-effective manner.

This background section introduces various aspects of the art that may be related to various aspects of the present disclosure described and/or claimed below. This discussion is intended to provide information to facilitate a better understanding of the various aspects of the present disclosure and the technical advantages provided. Accordingly, the statements made in this background section are to be read in this light, and are not admissions of prior art.

BRIEF DESCRIPTION

One aspect of the present disclosure is a method of evaluating a concrete sample that includes providing the concrete sample including a main body made of a concrete material comprising an aggregate and a paste; isolating a portion of the aggregate from the main body; isolating a portion of the paste from the main body and the isolated portion of the aggregate; separately analyzing the isolated portion of the aggregate and the isolated portion of the paste; and determining, based on the analyses of the isolated portions, whether the concrete material includes one or more sources of failure.

Another aspect of the present disclosure is a method of evaluating a concrete sample that includes providing the concrete sample including a main body made of a concrete material comprising an aggregate and a paste; isolating a portion of the aggregate from the main body; separately analyzing the main body and the isolated portion of the aggregate; and determining, based on the analyses of the main body and the isolated portion of the aggregate, whether the concrete material includes one or more sources of failure.

Another aspect of the present disclosure is a method of evaluating a concrete sample that includes providing the concrete sample including a main body made of a concrete material comprising an aggregate and a paste; isolating a portion of the paste from the main body; separately analyzing the main body and the isolated portion of the paste; and determining, based on the analyses of the main body and the isolated portion of the paste, whether the concrete material includes one or more sources of failure.

DETAILED DESCRIPTION OF THE DISCLOSURE

Figure 1:
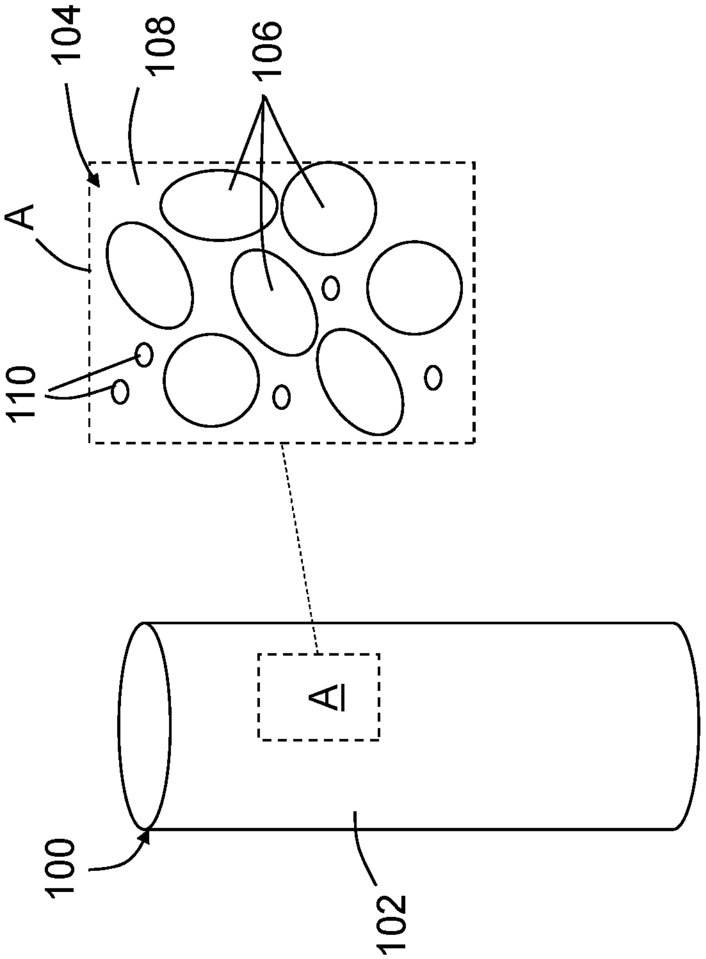
FIG. 1 is a schematic depiction of an example concrete core sample including multiple phases that are separated and individually analyzed in accordance with methods of the present disclosure.

FIG. 1 is a schematic depiction of a concrete core sample 100. In some embodiments, the concrete core sample 100 is a test specimen extracted from a hardened concrete structure, such as concrete pavement or a concrete building. In some embodiments, the concrete core sample 100 is extracted from the concrete structure using techniques known in the art, such as coring or drilling. For example, the concrete core sample 100 is extracted using a rotary cutting tool that includes drilling bits made of a superhard (e.g., diamond) material. In the schematic shown in FIG. 1, the concrete core sample 100 includes a substantially cylindrically shaped body 102. It will be appreciated that the size and shape of the concrete core sample 100 is not limited. In some embodiments, the concrete core sample 100 includes any size and/or shape that enables the concrete core sample 100 to be evaluated as described herein.

The concrete core sample 100 is made of a composite concrete material 104 (shown schematically in the enlarged Section A in FIG. 1). Suitably, the size and shape of the body 102 is such that the concrete material 104 included in the sample 100 is representative of the hardened concrete material that makes up the concrete structure from which the sample 100 is extracted. The concrete material 104 includes an aggregate 106 and a paste 108 (also referred to as a binder). In some embodiments, the aggregate 106 is referred to as a "first phase" or an "aggregate phase" of the concrete material 104 and the paste 106 is referred to as a "second phase" or a "paste phase" of the concrete material 104. In various embodiments, the materials used for the aggregate 106 and the paste 108 vary depending on the location of the cement source and its properties, quarry, and the intended application of the concrete structure.

The aggregate 106 is typically the primary constituent of the concrete material 104, and includes any suitable aggregate material used to form concrete. In some embodiments, the aggregate 106 includes particulate materials such as sand, gravel, crushed stone, sedimentary rock, recycled concrete, iron slag, and/or other materials suitable for use as a concrete aggregate. In various embodiments, the material used for the aggregate 106 varies depending on the approval of the quarry for its desired properties of the concrete structure, specifically the durability, strength, thermal properties, and/or density of the hardened concrete.

The paste 108 includes any suitable binding agent used to form concrete such as, for example, a mixture of cement (e.g., Portland cement), water, supplemental cementitious materials (e.g., fly ash), entrained and entrapped air. In various embodiments, a composition of the cement and supplemental cementitious material included in the paste 108 varies depending on its location and properties and the intended application of the concrete structure.

In some embodiments, the composite concrete material 104 includes other chemical and/or mineral admixtures (e.g., slag cement) depending on the intended application of the concrete structure. In some such embodiments, chemical or mineral admixtures are included in the concrete material 104 to provide various functions during preparing, handling, transporting, pouring, and/or setting the concrete material 104. For example, in some embodiments, the concrete material 104 includes chemical or mineral admixtures that facilitate delaying or accelerating the setting (or hardening) of the concrete material 104, targeting proper air entrainment in the concrete material 104, reducing a water-to-cement ratio in the paste 108, reducing shrinkage of the concrete material 104, providing a desired slump in the mixture used to form the concrete material 104, and/or inhibiting corrosion of the rebar in the concrete material 104, among other functions.

As is known in the art, to prepare the concrete material 104 that makes up the sample 100 (and the concrete structure), the paste 108 is made by mixing suitable proportions of the material(s) included in the cement together with a suitable amount of water. The paste 108 is mixed with additional proportions of the fine and/or coarse aggregate 106. In some embodiments, the mixture of the paste 108 and the aggregate 106 is mixed for a suitable duration to enable the cement and aggregate 106 to promote suitable hydration. The mixture is then poured in a desired location and shape and allowed to set or harden to form the concrete material 104. During mixing and hardening, air has the propensity to become entrained or entrapped, depending on the mixing, to form pores or voids 110 in the concrete material 104. In some embodiments, the pores 110 are referred to as a "third phase" or "pore phase" of the concrete material 104.

Over time and under certain situations, in some embodiments, constituents such as the aggregate 106, paste 108, and/or the pores 110 make the concrete material 104 susceptible to one or more deterioration mechanisms including, for example, corrosion of rebar reinforcement, sulfate attack, alkali-aggregate reactions, freeze-thaw durability issues, efflorescence, radiation, elevated heat of hydration, salt crystallization, and microbiological attack. Deterioration of the concrete material 104 jeopardizes the serviceability and safety of the concrete structure that includes the material 104, which, in some instances, leads to economic losses and catastrophic failures. In some embodiments, relatively high concentrations of such constituents that can make the concrete material 104 susceptible to one or more deterioration mechanisms are referred to as "sources of failure" of the concrete material 104.

In some embodiments, one or more of the sources of failure of the concrete material 104 includes relatively high concentrations of constituents that increase the alkali-aggregate reactivity and/or other negative mechanisms of the concrete material 104 by catalyzing or increasing the likelihood that alkali-silica reaction (ASR), alkali-carbonate reaction (ACR), and/or other reactions (e.g., sulfate attack) will occur in the concrete material 104. In various embodiments, constituents that contribute to the alkali-aggregate reactivity of the concrete material 104 are included in the body 102, the aggregate 106, the paste 108, and/or the pores 110 in a highly alkaline environment. For example, in some embodiments, ACR occurs when the aggregate 106 includes one or more of the following: calcium oxide (CaO), magnesium oxide (MgO), aluminum oxide ($Al_2O_3$), silicon dioxide ($SiO_2$), and potassium ($K_2O$) and sodium ($Na_2O$) oxides. Dedolomitization occurs when magnesium is removed from the mineral dolomite (calcium magnesium carbonate, $CaMg(CO_3)_2$), leaving behind the mineral calcite ($CaCO_3$) and periclase (magnesium carbonate, $MgCO_3$). In a concrete matrix, cement alkalis react with the mineral dolomite, catalyzing an alkali-aggregate reaction. Additionally, or alternatively, in some embodiments, this reaction leads to the formation of an alkali ($Na^+$, $K^+$, or $Li^+$) carbonate, magnesium hydroxide ($Mg(OH)_2$, or brucite), and calcite. The rates of both expansion and dedolomitization are functions of the calcite-dolomite ratio and texture of the rock in the concrete material 104. Aluminum oxide contributes to ACR since it indicates clay content, which absorbs moisture and subsequently can be a catalyst for further deleterious reaction. In some embodiments, absorption of moisture by the clay content allows accessibility for moisture to contribute to adverse reactions. ASR occurs when silicon dioxide or silica ($SiO_2$) from fine and/or coarse aggregate reacts with hydroxyl ions present in the concrete material (e.g., cement in the paste 108) to form a viscous, hygroscopic silicate gel (e.g., sodium silicate, $Na_2SiO_3$) that absorbs moisture and creates expansive pressure in the concrete material 104. Potassium and sodium oxide from the cement provide a source of alkalinity in the concrete material 104 for the reaction to occur. In some embodiments, the aggregate 106 includes dolomitic limestones that decompose in alkaline environments into brucite and calcite, as previously discussed. In some embodiments, the paste 108 and the pores 110 include constituents that are reactionary by-products of concrete hydration that can contribute to further reaction in the concrete material 104. In some embodiments, the paste 108 additionally or alternatively absorbs carbon dioxide ($CO_2$) and catalyzes carbonation thus forming magnesium carbonates ($MgCO_3$) and calcium carbonates ($CaCO_3$).

Figure 2:
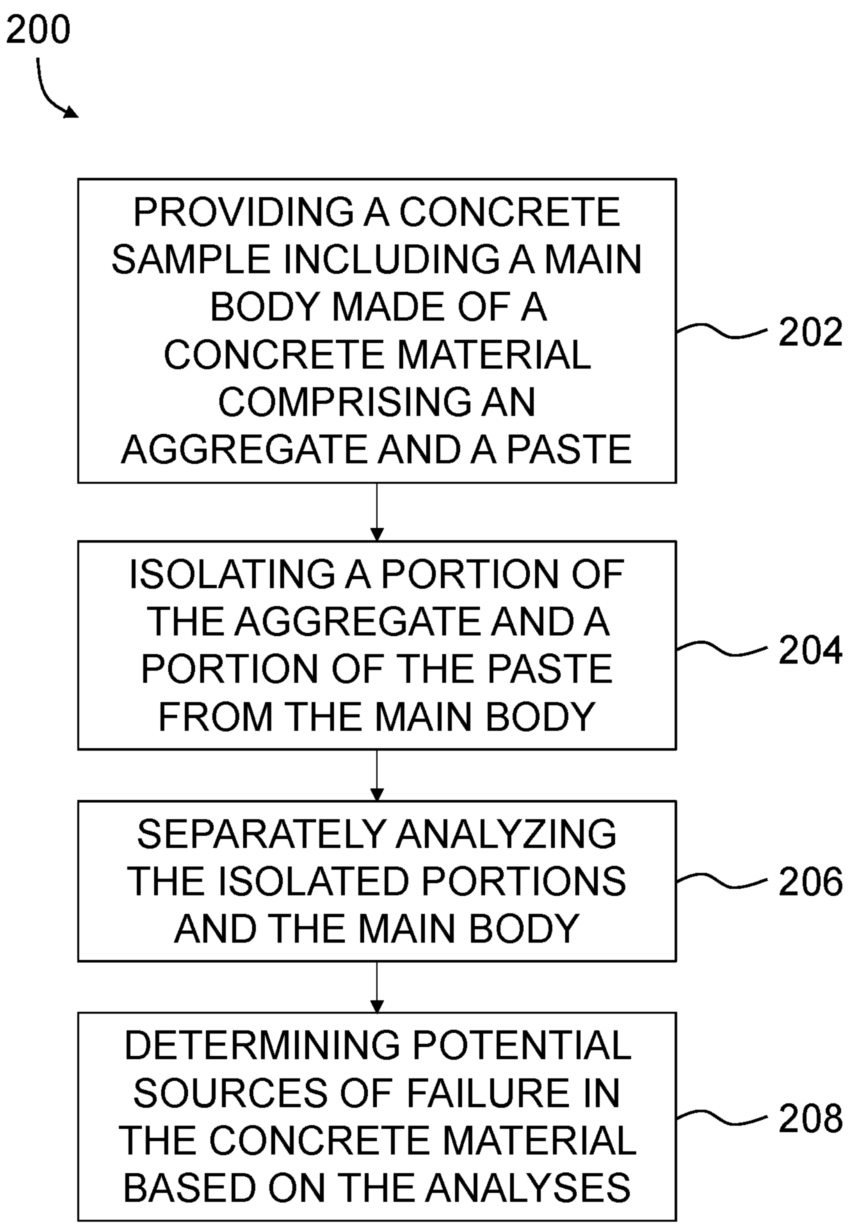
FIG. 2 is an exemplary method of evaluating a concrete sample, such as the concrete core sample of FIG. 1, using chemical analysis of separated phases of the concrete sample.

Referring now to FIG. 2, method 200 provides an example of evaluating a concrete sample, such as the concrete core sample 100 in FIG. 1, to determine whether the concrete sample includes one or more sources of failure. The method 200 includes providing 202 the concrete sample that includes a main body (e.g., the main body 102) made of a concrete material (e.g., the concrete material 104) that includes an aggregate (e.g., the aggregate 106) and a paste (e.g., the paste 108), as well as any chemical and/or mineral admixtures included in the concrete material and/or pores or voids (e.g., pores 110) that are formed in the concrete material. In some embodiments, the concrete sample 100 is provided 202 by obtaining a core sample from a concrete structure such as pavement or a building (e.g., using rotary cutting tools as described above). Alternatively, in some embodiments, the concrete sample is specifically manufactured for testing purposes. In some embodiments, the method 200 is used to identify actual sources of concrete failure (e.g., in instances where the concrete material has deteriorated over a shorter time than its life expectancy). In some embodiments, the method 200 is used to predict sources of concrete failure after the concrete material has been placed into use.

The method 200 also includes isolating 204 a portion of the aggregate from the main body and isolating 204 a portion of the paste from the main body and the isolated portion of the aggregate. In some embodiments, only the portion of the aggregate or the portion of the paste is isolated 204 from the main body. In some embodiments, isolating 204 the aggregate and/or paste portions from the main body includes meticulously extracting aggregate and/or paste from the concrete sample. In some such embodiments, this involves manually extracting aggregate and/or paste from the concrete sample using suitable techniques such as one or more of hand grinding, mortar and pestle, a hook and fork tip instrument, or another suitable tool or technique.

In some embodiments, the concrete sample is initially struck (e.g., with a hammer or other suitable tool) to break the sample into smaller pieces and to expose an interior of the sample (e.g., an inside of the concrete core sample 100 of FIG. 1). In some such embodiments, the concrete sample is seated on a solid surface (e.g., floor) prior to being struck. In some such embodiments, wax paper or another suitable sheet of non-stick, moisture-proof material is placed between the concrete sample and the surface to collect the pieces of the broken sample. The aggregate and paste are isolated 204 from the main body after breaking the sample down into smaller pieces, using the techniques described above for example. The pieces of the sample that remain after isolating 204 the aggregate and paste portions from the same are considered part of the "main body" of the sample. In some embodiments, some pieces of the sample are retained for further testing if needed and/or requested by the issuer. It will be understood that because only a portion of the aggregate and a portion of the paste are isolated 204, the main body that remains after the isolating 204 step includes the portions of the aggregate and paste that are not removed from the main body during the isolating 204 step.

In some embodiments, the aggregate that is isolated 204 from the main body of the concrete sample and the paste is observed under a stereoscope or other optical device to ensure that the isolated aggregate is substantially free from contaminants (e.g., from the pores or the paste). In some embodiments, isolating 204 the portion of the aggregate from the main body and from the paste includes removing any remaining contaminants from the aggregate (e.g., paste that is bound to aggregate). For example, in some embodiments, isolating 204 the portion of the aggregate from the main body and from the paste includes manually removing contaminants from the aggregate (e.g., using a hook and fork tip instrument) while visually inspecting the isolated aggregate under a stereoscope. Additionally, or alternatively, in some embodiments, isolating 204 the portion of the aggregate from the main body and from the paste includes grinding or agitating the aggregate (e.g., using a mortar and pestle) and selectively removing contaminants, such as remnants of the paste, from the ground aggregate while visually inspecting the ground aggregate under a stereoscope for verification and validity.

In some embodiments, the paste that is isolated 204 from the main body of the concrete sample and the aggregate is observed under a stereoscope or other optical device to ensure that the isolated paste is substantially free from contaminants (e.g., from the pores or the aggregate). In some embodiments, isolating 204 the portion of the paste from the main body and from the aggregate includes removing any remaining contaminants from the paste (e.g., aggregate that is bound to paste). For example, in some embodiments, isolating 204 the portion of the paste from the main body and from the aggregate includes manually removing contaminants from the paste (e.g., using a hook and fork tip instrument) while visually inspecting the isolated paste under a stereoscope. Additionally, or alternatively, in some embodiments, isolating 204 the portion of the paste from the main body and from the aggregate includes grinding or agitating the paste (e.g., using a mortar and pestle) and selectively removing contaminants, such as fine and/or coarse aggregate, from the ground paste while visually inspecting the ground paste under a stereoscope for verification and validity.

After the portions of the aggregate and the paste are isolated 204 from the main body and from one another, the isolated portions are separately analyzed 206. Initially, the isolated aggregate and the isolated paste are each prepared for analysis 206. In some embodiments, the isolated aggregate and the isolated paste are prepared for analysis 206 by grinding or agitating (e.g., using a mortar and pestle) the isolated portions into ground paste and ground aggregate. In some such embodiments, the ground paste and ground aggregate should have a fine consistency and are agitated through a #40 sieve.

In some embodiments, analysis 206 of the isolated aggregate and the isolated paste includes separately determining a moisture content in the isolated aggregate and paste. In some such embodiments, the moisture content is determined for the isolated aggregate and paste by separately weighing the isolated materials to determine an initial weight of each isolated material. In some embodiments, the isolated aggregate and paste are weighed using a 1+/−0.0005-gram scale on a calibrated balance for accuracy. The isolated aggregate and paste are then placed in heated chamber (e.g., a drying oven) while separately contained in suitable vessels (e.g., a porcelain crucible). The isolated aggregate and paste are dried in the heated chamber at a temperature and for a duration sufficient to remove moisture from the isolated aggregate and paste. In some embodiments, the isolated aggregate and paste are heated at a temperature of at least about 105° C. and for a duration of at least about 2 hours. After heating, the isolated aggregate and paste are allowed to cool and weighed again to determine a consistent post-heating weight of each isolated material. The moisture content is calculated for each of the isolated aggregate and paste based on a difference between the respective initial and post-heating weights.

In some embodiments, analysis 206 of the isolated aggregate and the isolated paste additionally or alternatively includes separately determining a loss on ignition (LOI) of the isolated aggregate and paste. In some embodiments, the determined LOI indicates the amount of moisture (e.g., water) and $CO_2$ present in the isolated aggregate and paste. In some embodiments, the LOI is determined for the isolated aggregate and paste after removing moisture from each of the isolated aggregate and paste and separately determining the moisture content of the isolated materials as described above. In some embodiments, the LOI of the isolated aggregate and paste is determined by separately weighing the isolated aggregate and paste to determine an initial weight of each isolated material. In some embodiments, the isolated aggregate and paste are weighed using a 1+/−0.0005-gram scale on a calibrated balance. The isolated aggregate and paste are then placed in heated chamber (e.g., a muffle furnace) that is at a suitable atmosphere (e.g., air or inert atmosphere) while separately contained in suitable vessels (e.g., a porcelain crucible). In some embodiments, the vessels are pre-ignited or pre-heated prior to receiving the respective isolated material. The isolated aggregate and paste are ignited in the heated chamber for a duration sufficient to remove moisture and $CO_2$ from the isolated materials. In some embodiments, the temperature and duration are selected based on certified test methods (e.g., ASTM C25). In some embodiments, the isolated aggregate and paste are heated at a temperature of at least about 950° C. and for a duration of at least about 2 hours. After heating, the isolated aggregate and paste are allowed to cool and weighed again to determine a post-heating weight of each isolated material. In some embodiments, the isolated aggregate and paste are cooled in a controlled atmosphere, such as water-free and/or $CO_2$-free atmosphere desiccator. The LOI of each of the isolated aggregate and paste is calculated based on a difference between the respective initial and post-heating weights. In some embodiments, the LOI for each of the isolated aggregate and paste is calculated as a percentage reduction in weight of the isolated material based on the respective initial and post-heating weights.

After the LOI and the moisture content of the isolated aggregate and paste are determined, the isolated materials are further analyzed 206 to separately determine a concentration of analytes that are indicative of chemical tracers associated with adverse reactions within the concrete material. In particular, the isolated aggregate and paste are separately analyzed 206 to determine the concentration of available aggregate and paste analytes. In some embodiments, the aggregate and paste analytes include similar and different analytes, which is consequence of the different materials used for the aggregate and the paste in the concrete material. In some embodiments, the aggregate and/or paste analytes include, but are not limited to including, one or more of calcium oxide, magnesium oxide, aluminum oxide, silicon dioxide, potassium oxide, and sodium oxide. In some embodiments, the paste analytes include, but are not limited to including, potassium oxide, sodium oxide, and carbon dioxide. In some embodiments, the aggregate and/or paste analytes include sulfur trioxide ($SO_3$) and iron oxide ($Fe_2O_3$).

In some embodiments, the isolated aggregate and paste are further analyzed 206 to determine the concentration of the aggregate and paste analytes using suitable analytical and instrumental techniques for detecting chemical elements and determining a compositional make-up of a material. In various embodiments, the concentration of the aggregate analytes in the isolated aggregate and the concentration of the paste analytes in the isolated paste are determined using spectroscopy, such as inductively coupled plasma optical emission spectroscopy (ICP-OES). In certain embodiments, the concentration of the aggregate analytes in the isolated aggregate and the concentration of the paste analytes in the isolated paste are determined using ICP-OES.

In some embodiments, the isolated aggregate and paste are prepared for spectroscopic analysis 206 to determine the respective concentration of aggregate analytes and paste analytes using a suitable sample preparation technique that enables accurate analysis using a spectrometer. For example, in some embodiments, the isolated aggregate and paste are prepared for spectroscopic analysis 206 using lithium metaborate fusion. In some such embodiments, the lithium metaborate fusion preparation of the isolated aggregate and paste is performed using a corrected weight of each isolated material based on the determined LOI. For example, in some embodiments, the corrected weight of each isolated material is calculated using the determined % LOI of the respective material multiplied by 0.2500+/−0.0005 grams. As an illustrative, non-limiting example, if the % LOI is 35%, take (100%-35%)=65%. From there, the corrected weight can be calculated as (0.2500 grams*0.65)=0.1625 grams. The corrected weight is then used for the lithium metaborate fusion, as described below.

In some embodiments, the isolated aggregate and paste are separately prepared for spectroscopic analysis 206 via lithium metaborate fusion as follows. A pre-determined amount of lithium metaborate (e.g., ¼ teaspoon) is added to each of two fusion vessels made of a suitable material (e.g., graphite crucibles), one fusion vessel for each isolated material. The lithium metaborate is compacted or pressed into a bed within the fusion vessel. In some embodiments, compaction of the lithium metaborate is performed using a test tube with a similar inner diameter as the fusion vessel, or using any other suitable technique. The % LOI of the isolated aggregate and paste is used to determine the corrected weight of each isolated material, as described above. The corrected weights of each of the isolated aggregate and paste are added to the respective fusion vessel into the bed of lithium metaborate. Once the isolated materials are added to their respective fusion vessel, another pre-determined amount (e.g., ¼ teaspoon) of lithium metaborate is added over the isolated material in each fusion vessel.

Once the fusion vessels are loaded with the lithium metaborate and respective isolated material as described above, the fusion vessels are placed into a heated chamber (e.g., a muffle furnace). The fusion materials are heated in their respective fusion vessels in the heated chamber at a temperature and for a duration sufficient to fuse the lithium metaborate and the isolated material. In some embodiments, the fusion materials are heated in their respective fusion vessel at a temperature of at least about 1000° C. and for a duration of at least about 30 minutes. After heating, the isolated fused bead of materials (or fused pellet) is immediately removed from the muffle furnace using specifically made tongs, swirled carefully in the graphite crucible, to avoid loss of sample, and placed into separate mixing vessels (e.g., a clear plastic beaker) containing a sufficient amount (e.g., 200 mL) of an acidic solution (e.g., 1:24 Nitric acid, $HNO_3$). In some embodiments, nitric acid is used since analytes are stable in this acid and will remain in solution. In some embodiments, the fused pellets are mixed in the acidic solution using a magnetic stir plate. Once the fused pellets have dissolved in the respective solution (e.g., after about 10 minutes of mixing), the fused pellet solutions are transferred to respective analysis vessels of pre-determined volume (e.g., a 250 mL volumetric flask). In some embodiments, the fused pellet solutions are filtered through a #41 (to remove carbon residue) during transfer to the analysis vessels. In some embodiments, a suitable amount of an internal standard is added to each analysis vessel (e.g., about 1 mL of Yttrium standard stock solution, 1000 ppm) before or after transfer of the fused pellet solution. The fused pellet solution-internal standard mixture is then diluted to volume, and spectroscopy (e.g., ICP-OES) is then used determine the concentration of the aggregate and paste analytes using numerous high and low concentration of certified reference materials to create a calibration line for each measured analyte on the ICP-OES under a prescribed test template.

In some embodiments, the method 200 also includes analyzing 206 the main body of the concrete sample that remains after isolating 204 the portions of the aggregate and paste. In some such embodiments, analyzing 206 the main body in addition to the isolated aggregate and paste provides a comprehensive chemical analysis for determining whether the concrete sample includes one or more sources of failure, as the analysis 206 includes determining the compositional make-up and chemical elements that are included in multiple phases of the concrete sample, for example, the aggregate, the paste, and the pores.

In some embodiments, analyzing 206 the main body of the concrete sample includes performing a water solubility analysis on the main body. The water solubility analysis is performed to determine a concentration of water-soluble elements (e.g., tracers) included in the main body. In some embodiments, such water-soluble elements, also referred to as main body analytes, are included in the pores of the main body, or in the aggregate and/or paste that was not isolated 204 from the main body. In some embodiments, the main body analytes, like the aggregate and paste analytes, are indicative of reactive potential (e.g., alkali-aggregate reactivity) of the concrete material. In some embodiments, the main body analytes include similar and/or different analytes as the aggregate and paste analytes. In some embodiments, the main body analytes include, but are not limited to including, one or more of the following: calcium oxide (CaO), magnesium oxide (MgO), sulfur trioxide ($SO_3$), aluminum oxide ($Al_2O_3$), silicon dioxide ($SiO_2$), and potassium ($K_2O$) and sodium ($Na_2O$) oxides.

In some embodiments, performing the water solubility analysis on the main body includes submersing the main body in water (e.g., deionized water) in a water-solubility analysis vessel (e.g., a beaker) of suitable volume (e.g., 2000 mL). The submersed main body and water are heated to a suitable temperature to bring the water to a boil and for a duration sufficient to solubilize and dissolve the main body analytes in the water. In some embodiments, the submersed main body and water are heated to a slight boil (e.g., at least about 100° C.) for at least about 5 minutes, or at least about 30 minutes, to allow the main body analytes to dissolve in the water. In some embodiments, the heating is performed using a hot plate. The submersed main body and the water are then allowed to cool in the water-solubility analysis vessel. After cooling, the water is separated from the main body and transferred into one or more spectroscopy vessels (e.g., 70 mL polyethylene digestion vessels) and the spectroscopy vessels are capped. The separated water is then analyzed to determine a concentration of the solubilized main body analytes in the water. In some embodiments, the analysis of the separated water is performed using ICP-OES against a blank solution (e.g., 1:24 $HNO_3$) and semi-quantitative standards (e.g., 10 ppm for each analyte in solution). In some embodiments, the separated water is diluted as needed depending on the specific analyte concentration during the analysis.

It will be appreciated that the above steps 202-206 include additional, fewer, or other actions in various embodiments of the method 200. In some embodiments of the method 200, the aggregate is isolated 204 from the main body and analyzed 206 separately from the main body, and the paste is neither isolated 204 nor analyzed 206 separately from the main body. In other embodiments of the method 200, the paste is isolated 204 from the main body and analyzed 206 separately from the main body, and the aggregate is neither isolated 204 nor analyzed 206 separately from the main body. In some embodiments of the method 200, the aggregate and the paste are each isolated 204 from the main body and from each other, and the isolated aggregate and paste are analyzed 206 separately from each other, and the main body is not analyzed 206. In some embodiments of the method 200, the aggregate and the paste are isolated 204 from the main body, but not from each other, and the aggregate and paste are analyzed 206 together and separately from the main body analysis. Suitably, the method 200 includes separately analyzing 200 at least two phases (e.g., at least two of the isolated aggregate, the isolated paste, and the main body) of the concrete sample to provide a comprehensive chemical analysis of the concrete material.

The method 200 also includes determining 208 whether the concrete material includes one or more potential sources of failure. The determination 208 is based on the analyses 206 of the isolated aggregate, the isolated paste, and/or the main body. In some embodiments, one or more sources of concrete failure are determined 208 based on the concentration of one or more of the aggregate analytes, the paste analytes, and/or the main body analytes. In some such embodiments, the determination 208 includes consideration of all available chemical tracers identified in the analyses 206 and forming a conclusion based on the available data. In various embodiments, defined analyte concentrations used for determining 208 one or more sources of failure vary depending on the analyte and how it pertains to the findings. In some embodiments, the analysis for a particular analyte is determined based on a calculated concentration of the analyte which could contribute to the potential for ASR, ACR, or other reactions occurring in the concrete material 104 that cause concrete failure.

In some embodiments, the one or more sources of concrete failure are determined 208 based on a total moisture and/or a total alkali in the paste. In some such embodiments, the total moisture is calculated based on the LOI of the isolated paste and the $CO_2$ concentration in the isolated paste determined during analysis 206 of the isolated paste as described above. Additionally or alternatively, in some such embodiments, the total alkali in the paste is calculated based on the determined concentration of sodium-based paste analytes and potassium-based paste analytes determined during analysis 206 of the isolated paste as described above. For example, the total alkali in the paste is calculated by the equation ($Na_2O$+0.658*$K_2O$) based on the determined concentration of sodium oxide ($Na_2O$) and potassium oxide ($K_2O$) determined during analysis 206 of the isolated paste as described above.

The above-described embodiments provide methods of evaluating concrete that include a comprehensive chemical analysis of the concrete, facilitate accurately predicting concrete failure and/or determining actual sources of failure, and doing so in a cost-effective manner. In this way, the embodiments described herein present several technical benefits and bypass several technical limitations and challenges in the art. For example, technical effects provided by the present disclosure include, but are not limited to only including, a) evaluating and accurately evaluating concrete samples using less-costly equipment compared to expensive instrumentation (e.g., scanning electron microscopes) used in existing methods, thereby reducing costs associated with diagnosing concrete failure, b) providing a comprehensive, multi-phase analysis of the concrete that takes into account the aggregate as well as alkaline materials of the concrete to assess potential and actual sources of concrete failure, c) providing a novel approach to identifying an overall thumbprint of the concrete core chemistry, d) facilitating new ways to solve concrete problems quickly and efficiently, e) keeping all concrete testing internal by using readily available in-house laboratory resources to determine sources of failure, thereby avoiding the need to outsource lab work which is inefficient and increases costs and time, f) simplifying the evaluation process, thereby enabling a repeatable and consistent step-by-step process, g) improving safety by avoiding the use of harsh chemicals/concentrated acids, replacing these chemicals with water and weak acid solutions (e.g., 1:24 $HNO_3$), and h) providing a readily distributable concrete evaluation test method that can be used nation and world-wide to prevent catastrophic failures and fatalities.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1. Standard Test Method for Chemical Analysis of Concrete Cores by Extraction and Solubility Scope. This method evaluates concrete cores by concentrating on three phases (aggregate, paste and pores/voids) to assist and/or verify the reason(s) for the failure.

Summary of Method. Aggregate and paste samples are meticulously extracted from the concrete core sample. The aggregate and paste samples are analyzed under a stereoscope for any contamination of paste on the aggregate and aggregate in the paste. The samples are crushed and sieved through a #40 sieve. The minus 40 material is evaluated by instrumental analysis for chemical tracers (indicators) potentially associated with the concrete failure. The remaining portions of the concrete core sample(s) are submerged in deionized water and boiled on a hot plate. A semi-quantitative analysis is performed on the extract for water-soluble elements (tracers) that could be potentially associated with the failure.

Equipment and Reagents: 1) Glass beaker, 2000-mL; 2) Nitric Acid ($HNO_3$), Certified A.C.S Grade; 3) Deionized water, generated through Reverse Osmosis System; 4) Mortar and pestle; 5) Hammer; 6) No. 40 sieve, conforming to ASTM E-11 Specification; 7) Hook/Straight Fork Tip, 5½" in length; 8) Brown waxed paper, for sample collection; 9) Graphite crucibles, 8-mL capacity; 10) Clear plastic beakers (Polypropylene), 400-mL capacity; 11) Magnetic stirring bars, length of bars should be ½" less than the inside diameter of the beaker; 12) Lithium Metaborate (LiBO2), Reagent Grade, Anhydrous; 13) Yttrium Stock Solution, 1000 mg/L (ppm); 14) Inductively Coupled Plasma Optical Emission Spectrophotometer (ICP-OES), capable of internal standard correction; 15) Filter paper, rapid filtering, #41 or equivalent; 16) Filter funnel; 17) Semi-Quantitative Standards, traceable to NIST, 10 ppm; 18) Muffle furnace, 1000° C. capability; 19) Polyethylene digestion vessel with cap, 70-mL capacity; 20) Porcelain crucible, 15-mL capacity.

Procedure 1. Place brown wax paper on floor and set the concrete core sample in the middle of the paper. Strike the sample with a hammer to expose the inside of the core. Examine the sample and choose section(s) to extract aggregate and paste from the concrete core. Sample a minimum of 5 large pieces of aggregate and paste to retain separately for further evaluation. Using the Hook Fork Tip instrument, chip off excess paste off of extracted aggregate and use a stereoscope to verify aggregate is not contaminated and retain. For extracted paste, use mortar and pestle to gently agitate paste to isolate any aggregate and sand in the paste. View under stereoscope, remove aggregate and sand from the paste if present, and retain. Use mortar and pestle to break each individual sample into a fine consistency and sieve through a #40 sieve. Repeat, in necessary, and retain for further testing. Determine the moisture content on paste and aggregate separately in a 105° C. drying oven for 2 hours on a 1+/−0.0005-gram sample in a porcelain crucible. Cool, weigh, record and calculate.

Determine the % Loss on Ignition (LOI) on the moisture free aggregate and paste samples at 950° C. in a muffle furnace for 2 hours. Cool, weigh, record and calculate. Use % LOI result to calculate corrected weight from 0.2500+/−0.0005 grams. As an example, if the % LOI is 35%, take (100%-35%)=65%. From there, take (0.2500 grams*0.65) =0.1625 grams. This is the corrected weight and is used to fuse with lithium metaborate.

For fusion of aggregate and paste, add ¼ teaspoon of lithium metaborate to 2 graphite crucibles and use a test tube with the same inner diameter of the crucible, press down the lithium metaborate to make a bed. Use the % LOI of the aggregate and paste, and determine corrected weight, as described above, to weigh into the bed of lithium metaborate in the crucible. Once weighed up, add another ¼ teaspoon of lithium metaborate over the sample in the crucible. Load crucibles into a 1000° C. muffle furnace for 30 minutes and drop fused pellet into a clear, plastic beaker containing 200-mL of 1:24 $HNO_3$. Place beaker on a stir plate and stir for at least 10 minutes until dissolved. Add 1-mL of yttrium to a 250-mL volumetric flask and filter through a #41 filter into flask. Dilute to volume and analyze on ICP-OES using prescribed test template set up for aggregate analysis.

Procedure 2. Take remaining pieces of the concrete core sample, after extraction of aggregate and paste, and place in a 2000-mL beaker. Cover sample with deionized water and boil on hot plate for at least 5 minutes, or at least 30 minutes. Take beaker off hot plate and cool to room temperature. Pour water extract into a 3×70-mL polyethylene digestion vessels and cap. Analyze extract on ICP-OES with blank (1:24 $HNO_3$) and 10 ppm semi-quantitative standards. Dilute, if needed, and print report.

Example 2. First Exemplary Chemical Analysis of Concrete by Extraction and Solubility According to the Standard Test Method of Example 1

Concrete core samples (samples 1-8 in Tables 1-3) were submitted from 8 different locations in Missouri, USA where pavement had the most amount of distress. The purpose was to identify the cause of the significant pavement deterioration occurring at these specific locations. Representative samples of aggregate were extracted from each core of the 8 different locations to check chemical components. The chemistry of the aggregates can facilitate determining the sources of deterioration and concrete failure. From the analysis, ACR was studied intently since aggregate chemistry showed potential expansive properties at all 8 locations. This was based on the CaO/MgO (dolomitic limestone) ratio versus $Al_2O_3$ (clay content) graph. Potassium oxide, $K_2O$, is another indicator at certain concentrations to contribute to ACR. The chemical analysis of CaO, MgO, $Al_2O_3$, $SiO_2$, and $K_2O$ from the extracted aggregate is shown below in Table 1.

TABLE 1

Analysis of Extracted Aggregate from Concrete Pavement

| Sample (location) | $SiO_2$ (%) | $Al_2O_3$ (%) | CaO (%) | MgO (%) | Ratio | Within Potential Expansive Parameter? |
|---|---|---|---|---|---|---|
| 1 | 5.08 | 0.69 | 46.54 | 4.7 | 9.9 | Yes |
| 2 | 5.8 | 1.25 | 47.08 | 3.86 | 12.2 | Yes |
| 3 | 7.29 | 1.41 | 40.13 | 9.25 | 4.34 | Yes |
| 4 | 6.82 | 1.48 | 44.86 | 5.26 | 8.53 | Yes |
| 5 | 5.63 | 0.9 | 45.1 | 5.71 | 7.9 | Yes |
| 6 | 6.48 | 1.34 | 42.16 | 8.52 | 4.95 | Yes |
| 7 | 4.65 | 0.74 | 44.13 | 6.83 | 6.46 | Yes |
| 8 | 3.28 | 0.59 | 49.15 | 3.01 | 16.33 | Yes |
| | $K_2O$ (%) | LOI (%) | $CO_2$ (%) | | | |
| 1 | 0.14 | 41.71 | 41.2 | | | |
| 2 | 0.18 | 40.85 | 41.32 | | | |
| 3 | 0.33 | 40.76 | 40.59 | | | |
| 4 | 0.3 | 40.32 | 39.92 | | | |
| 5 | 0.21 | 41.23 | 41.45 | | | |

TABLE 1-continued

Analysis of Extracted Aggregate from Concrete Pavement

| Sample (location) | $SiO_2$ (%) | $Al_2O_3$ (%) | CaO (%) | MgO (%) | Ratio | Within Potential Expansive Parameter? |
|---|---|---|---|---|---|---|
| 6 | 0.27 | 41.07 | 41.15 | | | |
| 7 | 0.13 | 41.87 | 42.17 | | | |
| 8 | 0.12 | 41.76 | 41.53 | | | |

The paste analysis measures moisture availability and total alkali content, which are variables associated with ACR. The paste was tested for LOI, $CO_2$, $Na_2O$ and $K_2O$. Moisture availability and total alkali content calculation are included below in Table 2.

TABLE 2

Analysis of Extracted Paste from Concrete Pavement

| Sample (location) | $Na_2O$ (%) | $K_2O$ (%) | Total Alkali ($Na_2O + 0.658 * K_2O$) |
|---|---|---|---|
| 1 | 0.48 | 0.86 | 1.05 |
| 2 | 0.55 | 0.84 | 1.1 |
| 3 | 0.66 | 1.23 | 1.47 |
| 4 | 0.42 | 0.51 | 0.76 |
| 5 | 0.59 | 1.01 | 1.25 |
| 6 | 0.47 | 0.79 | 0.99 |
| 7 | 0.57 | 0.91 | 1.17 |
| 8 | 1.08 | 1.77 | 2.24 |
| | LOI (%) | $CO_2$ (ppm) | Total Moisture ($LOI - CO_2$) |
| 1 | 19.52 | 3.77 | 15.75 |
| 2 | 17.45 | 1.75 | 15.7 |
| 3 | 15.72 | 4.84 | 10.88 |
| 4 | 23.4 | 3.88 | 19.52 |
| 5 | 18.68 | 4.25 | 14.43 |
| 6 | 20.35 | 5.57 | 14.78 |
| 7 | 19.48 | 4.9 | 14.58 |
| 8 | 12.51 | 5.3 | 7.21 |

Chemical analysis by solubility is the last step of the concrete core analysis. Representative samples from each of the 8 cores were submerged in distilled water and boiled for 30 minutes. This method is done to flush out any potential chemical tracers that assist in pinpointing the cause of the pavement distress. A semi-quantitative analysis measures the water extract from the core, looks at over 60 analytes and provides intensity values based on the concentration of analytes present in the water extract. The water extract results have been included in below in Table 3.

TABLE 3

Water-Solubility Analysis of Concrete Core

| Sample (location) | $SiO_2$ (ppm) | MgO (ppm) | $Na_2O$ (ppm) | $K_2O$ (ppm) |
|---|---|---|---|---|
| 1 | 38 | 0 | 39 | 22 |
| 2 | 5 | 0 | 45 | 18 |
| 3 | 7 | 0 | 39 | 29 |
| 4 | 2 | 0 | 25 | 21 |
| 5 | 2 | 0 | 25 | 15 |
| 6 | 5 | 0 | 23 | 11 |
| 7 | 12 | 0 | 24 | 14 |
| 8 | 26 | 0 | 23 | 12 |

From the 3 components (Aggregate, paste and pores) of the concrete matrix, the aggregate and paste analysis showed the most common trend toward ACR. However, the water extract from the solubility phase of testing showed little to no analyte concentration that contributes to ACR or ASR. The pavement deterioration was extensive and no signs of ASR gel and/or map cracking consistent with ACR. Even though, air void analysis was not performed on these cores, low air causing significant freeze thaw durability issues were prevalent in each of these locations.

Example 3. Second Exemplary Chemical Analysis of Concrete by Extraction and Solubility According to the Standard Test Method of Example 1

Concrete core samples showing signs of pavement distress were analyzed. The initial analysis on the aggregate indicated that the chemistry contained factors potentially contributing to ACR. The original chemical analysis on the aggregate is shown below in Table 4. Previously, the standard operating procedure (SOP) was to monitor CaO/MgO ratio versus $Al_2O_3$ and determine whether parameters fall within aggregate samples of similar chemistry deemed potentially expansive. ASTM C-586 Rock Cylinder Test was used to create this model for determining reactive aggregates and, if needed, pursuing concrete testing per ASTM C-1105. Through internal chemical and concrete testing, $K_2O$ has been identified as an indicator at certain concentrations to contribute to ACR. ACR occurs when dolomitic limestones decompose into calcite (Ca based), brucite (Mg based) and an alkali element (K based).

TABLE 4

| Chemical Analysis According to Previous SOP (%) | | | | |
|---|---|---|---|---|
| $Al_2O_3$ | CaO | MgO | $Na_2O$ | $K_2O$ |
| 1.38 | 42.18 | 7.22 | 0.026 | 0.363 |

One objective was to extract the aggregate from the paste in the concrete core. The goal was to retain representative samples throughout the core, visually inspect the aggregate under the stereoscope for paste contamination, crush, split, pass through #40 sieve into a pan and run complete chemical analysis. Instrumental and analytical methods were conducted. From the analysis of the aggregate, the chemistry changed significantly. The chemical analysis report is included in Table 5 below.

TABLE 5

| Chemical Analysis According to Exemplary Method using Extracted Aggregate (%) | | | | |
|---|---|---|---|---|
| $Al_2O_3$ | CaO | MgO | $Na_2O$ | $K_2O$ |
| 2.08 | 32.29 | 13.74 | 0.088 | 0.515 |

As shown in Tables 4 and 5, there was a significant change in the chemistry of the aggregate from the initial analysis to the extraction from the ACR core. ACR was observed from decomposition of aggregate.

The next step was to isolate the paste for chemical analysis and measure certain indicators attributed to the suspected ACR. Moisture availability and high alkali content are prevalent factors of ACR expansion in concrete. The paste was isolated from the aggregate meticulously using a stereoscope to visually identify any contamination present. The presence of silica sand (fine aggregate) causes additional issues since high amounts of $SiO_2$ in sand prevents the paste from fusing with lithium metaborate. The majority of $SiO_2$ can be removed from the sample by passing it through a #40 sieve in a pan. The material was tested for Na, K, LOI, and $CO_2$. The calculation for moisture present is LOI-$CO_2$ and total alkali content is calculated by taking Na+ (0.658*$K_2O$). The chemical analysis is included in Table 6 below.

TABLE 6

| Chemical Analysis According to Exemplary Method using Extracted Aggregate (%) | | | | | |
|---|---|---|---|---|---|
| LOI | Na | K | $CO_2$ | Total Alkali | Moisture |
| 18.71 | 0.74 | 1.623 | 5.63 | 1.81 | 13.08 |

The expansion of ACR concrete is related to moisture availability and high alkali content. These factors are prevalent in this sample.

In the foregoing specification and the following claims, reference is made to several terms, which have the following meanings.

The singular forms "a," "an," "the," and "said" include plural references unless the context clearly dictates otherwise.

The terms "comprising," "including," and "having" are intended to be inclusive and mean that there may be additional elements other than the listed elements.

"Optional" or "optionally" means that the subsequently described event or circumstance may or may not occur, and that the description includes instances where the event occurs and instances where it does not.

References to "one embodiment" are not intended to be interpreted as excluding the existence of additional embodiments that also incorporate the recited features. Moreover, although specific features of various embodiments described herein may be shown in some drawings and not in others, this is for convenience only. In accordance with the principles of the present disclosure, any feature of a drawing and/or embodiment described herein may be referenced and/or claimed in combination with any feature of any other drawing and/or embodiment described herein. Furthermore, unless explicitly stated to the contrary, embodiments "including" or "having" an element or a plurality of elements having a particular property may include additional such elements not having that property.

This written description uses examples to disclose the embodiments, including the best mode, and to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of evaluating a concrete sample, the method comprising:

providing the concrete sample including a main body made of a concrete material comprising an aggregate and a paste;

isolating a portion of the aggregate from the main body;

isolating a portion of the paste from the main body and the isolated portion of the aggregate;

separately analyzing the isolated portion of the aggregate and the isolated portion of the paste; and determining, based on the analyses of the isolated portions, whether the concrete material includes one or more sources of failure;

wherein analyzing the isolated portion of the aggregate comprises determining loss on ignition of the aggregate; and wherein analyzing the isolated portion of the paste comprises determining loss on ignition of the paste.

2. The method of claim 1, further comprising:

separately analyzing the main body after isolating the portion of the aggregate and the portion of the paste from the main body; and determining, based on the analyses of the isolated portions and the main body, whether the concrete material includes the one or more sources of failure.

3. The method of claim 2, wherein analyzing the main body comprises performing a water solubility analysis on the main body.

4. The method of claim 3, wherein performing the water solubility analysis on the main body comprises:

submersing the main body in water;

heating the submersed main body and water for a duration sufficient to solubilize analytes in the main body to dissolve in the water;

separating the water from the main body after heating; and analyzing the separated water to determine a concentration of the solubilized analytes in the water.

5. The method of claim 4, wherein the solubilized analytes include one or more of $SiO_2$, MgO, $Na_2O$, and $K_2O$.

6. The method of claim 1, wherein analyzing the isolated portion of the aggregate further comprises determining a concentration of aggregate analytes in the aggregate that are indicators for alkali-aggregate reactivity.

7. The method of claim 6, wherein the aggregate analytes include one or more of CaO, MgO, $Al_2O_3$, $SiO_2$, $Na_2O$, and $K_2O$.

8. The method of claim 1, wherein analyzing the isolated portion of the paste further comprises determining a concentration of paste analytes in the paste that are indicators for alkali-aggregate reactivity.

9. The method of claim 8, wherein the paste analytes include one or more of $CO_2$, $Na_2O$, and $K_2O$.

10. The method of claim 9, further comprising determining a total alkali of the paste based on the determined concentration of the paste analytes.

11. The method of claim 1, further comprising determining a concentration of $CO_2$ in the paste and, based on the determined loss on ignition of the paste and the determined concentration of $CO_2$ in the paste, determine a total moisture content in the paste.

12. A method of evaluating a concrete sample, the method comprising:

providing the concrete sample including a main body made of a concrete material comprising an aggregate and a paste;

isolating a portion of the aggregate from the main body;

separately analyzing the main body and the isolated portion of the aggregate; and determining, based on the analyses of the main body and the isolated portion of the aggregate, whether the concrete material includes one or more sources of failure;

wherein analyzing the main body comprises performing a water solubility analysis on the main body, the water solubility analysis comprising:

submersing the main body in water;

heating the submersed main body and water for a duration sufficient to solubilize analytes in the main body to dissolve in the water;

separating the water from the main body after heating; and analyzing the separated water to determine a concentration of the solubilized analytes in the water, wherein the solubilized analytes include one or more of SiO2, MgO, Na2O, and K2O.

13. The method of claim 12, wherein analyzing the isolated portion of the aggregate comprises determining a concentration of aggregate analytes in the aggregate that are indicators for alkali-aggregate reactivity, wherein the aggregate analytes include one or more of CaO, MgO, $Al_2O_3$, $SiO_2$, $Na_2O$, and $K_2O$.

14. A method of evaluating a concrete sample, the method comprising:

providing the concrete sample including a main body made of a concrete material comprising an aggregate and a paste;

isolating a portion of the paste from the main body;

separately analyzing the main body and the isolated portion of the paste; and determining, based on the analyses of the main body and the isolated portion of the paste, whether the concrete material includes one or more sources of failure;

wherein analyzing the main body comprises performing a water solubility analysis on the main body, the water solubility analysis comprising:

submersing the main body in water;

heating the submersed main body and water for a duration sufficient to solubilize analytes in the main body to dissolve in the water;

separating the water from the main body after heating; and analyzing the separated water to determine a concentration of the solubilized analytes in the water, wherein the solubilized analytes include one or more of SiO2, MgO, Na2O, and K2O.

15. The method of claim 14, wherein analyzing the isolated portion of the paste comprises determining a concentration of paste analytes in the paste that are indicators for alkali-aggregate reactivity, wherein the paste analytes include one or more of $CO_2$, $Na_2O$, and $K_2O$; wherein the method further comprises determining a total alkali of the paste based on the determined concentration of the paste analytes.

16. The method of claim 14, wherein analyzing the isolated portion of the paste comprises determining loss on ignition of the paste; wherein the method further comprises determining a concentration of $CO_2$ in the paste and, based on the determined loss on ignition of the paste and the determined concentration of $CO_2$ in the paste, determine a total moisture content in the paste.

* * * * *